(12) United States Patent
Okamoto et al.

(10) Patent No.: US 9,221,740 B2
(45) Date of Patent: Dec. 29, 2015

(54) METHOD FOR PRODUCING CARBONATE COMPOUND AND METHOD FOR PRODUCING AROMATIC POLYCARBONATE

(71) Applicant: Asahi Glass Company, Limited, Tokyo (JP)

(72) Inventors: Hidekazu Okamoto, Tokyo (JP); Atsushi Fujimori, Tokyo (JP); Toru Takahashi, Tokyo (JP); Keisuke Shimokawa, Tokyo (JP); Atsushi Hirashima, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/617,586

(22) Filed: Feb. 9, 2015

(65) Prior Publication Data

US 2015/0152037 A1   Jun. 4, 2015

Related U.S. Application Data

(63) Continuation of application No. PCT/JP2013/071279, filed on Aug. 6, 2013.

(30) Foreign Application Priority Data

Aug. 10, 2012   (JP) ................. 2012-178327

(51) Int. Cl.
| | |
|---|---|
| *C08G 64/00* | (2006.01) |
| *C07C 68/00* | (2006.01) |
| *C07C 68/08* | (2006.01) |
| *C08G 64/26* | (2006.01) |
| *C08G 64/06* | (2006.01) |
| *C08G 64/30* | (2006.01) |
| *C08G 63/02* | (2006.01) |

(52) U.S. Cl.
CPC ............. *C07C 68/00* (2013.01); *C07C 68/08* (2013.01); *C08G 64/06* (2013.01); *C08G 64/266* (2013.01); *C08G 64/307* (2013.01)

(58) Field of Classification Search
CPC ..................................... C08G 64/307
USPC ................... 528/196, 198, 271, 272
See application file for complete search history.

(56) References Cited

U.S. PATENT DOCUMENTS

| | | | | |
|---|---|---|---|---|
| 4,353,831 | A | * | 10/1982 | Strege et al. ............ 549/229 |
| 5,091,543 | A | * | 2/1992 | Grey ...................... 549/228 |
| 2010/0240912 | A1 | | 9/2010 | Okamoto et al. |
| 2010/0249436 | A1 | | 9/2010 | Okamoto et al. |

FOREIGN PATENT DOCUMENTS

| | | |
|---|---|---|
| JP | S60-197639 A | 10/1985 |
| JP | H07-206847 A | 8/1995 |
| JP | 2011-040311 A | 2/2011 |
| WO | WO-2009/072501 A1 | 6/2009 |
| WO | WO-2009/072502 A1 | 6/2009 |
| WO | WO-2010/001870 A1 | 1/2010 |
| WO | WO-2010/140572 A1 | 12/2010 |
| WO | WO-2011/120198 A1 | 10/2011 |

OTHER PUBLICATIONS

International Search Report dated Nov. 5, 2013 issued in Application No. PCT/JP2013/071279.
Srivastava, et al., "Fe—Zn double-metal cyanide complexes as novel, solid transesterfication catalysts," Journal of Catalysis, 241 (2006), pp. 34-44.

* cited by examiner

*Primary Examiner* — Terressa Boykin
(74) *Attorney, Agent, or Firm* — Foley & Lardner LLP

(57) ABSTRACT

The present invention relates to a method for producing a carbonate compound containing: a first step of reacting a compound represented by the following Formula (1) with a compound represented by the following Formula (21) or a compound represented by the following Formula (22) to obtain a reaction mixture containing a carbonate compound, and a second step of bringing the reaction mixture containing a carbonate compound into contact with a strongly basic compound,

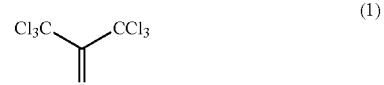
(1)

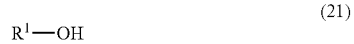

(21)

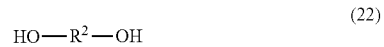

(22)

in which $R^1$ represents a monovalent organic group, and $R^2$ represents a divalent organic group.

7 Claims, 1 Drawing Sheet

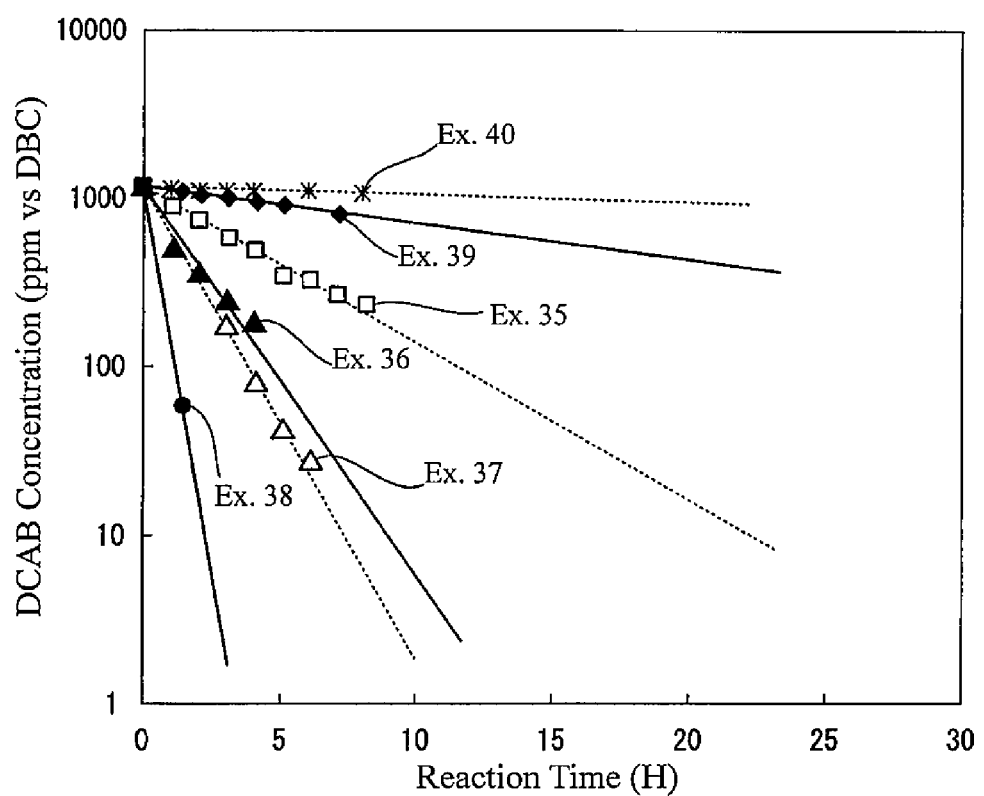

METHOD FOR PRODUCING CARBONATE COMPOUND AND METHOD FOR PRODUCING AROMATIC POLYCARBONATE

CROSS REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/071279 filed on Aug. 6, 2013, which is based upon and claims the benefit of priority of Japanese Application No. 2012-178327 filed on Aug. 10, 2012, the entire contents of which are hereby incorporated by reference in their entireties.

TECHNICAL FIELD

The present invention relates to a method for producing a carbonate compound and aromatic polycarbonate.

BACKGROUND ART

Aromatic polycarbonates have been widely used in many fields, as engineering plastics excellent in thermal resistance, impact resistance, transparency, and the like.

As a method for producing aromatic polycarbonate, for examples, the following methods are known.

(i) A method of causing interfacial polycondensation of bisphenol A with phosgene in the presence of an alkaline catalyst (phosgene process).

(ii) A method of causing melt-polycondensation of bisphenol A with diphenyl carbonate (ester exchange process) (Patent Document 1).

In the method (i), the reaction proceeds at a low temperature, so colorless transparent polycarbonate can be obtained. However, this method has problems that toxic phosgene is used; inorganic salts such as sodium chloride produced as a by-product by the reaction should be removed by washing; due to the use of a solvent such as methylene chloride, complicated processes such as polymer purification and recovery of the solvent are required after the reaction; and the like.

On the other hand, the method (ii) has advantages that phosgene is not used; inorganic salts are not by-produced by the reaction; a solvent does not need to be used and hence it is easy to separate polycarbonate from the reaction system; and the like.

As a method for producing diphenyl carbonate, the following methods are known, similarly to the method for producing aromatic polycarbonate.

(iii) A method of reacting phenol with phosgene (phosgene process).

(iv) A method of reacting phenol with a carbonate compound (dialkyl carbonate or cyclic carbonate) (ester exchange process).

As the method for producing diphenyl carbonate, the method (iv) not using phosgene is preferable in view of the reduction in environmental load and of safety.

As a method for producing a carbonate compound, the following methods are known.

(v) A method for producing cyclic carbonate by reacting carbon dioxide gas with alkene oxide in the presence of a catalyst (Patent Document 2).

(vi) A method for producing dialkyl carbonate or cyclic carbonate by reacting phosgene with an alcohol (Patent Document 3).

(vii) A method for producing dialkyl carbonate by causing an ester exchange reaction between cyclic carbonate or dimethyl carbonate and alcohol in the presence of a catalyst for an ester exchange reaction (Non-Patent Document 1).

(viii) A method for producing dialkyl carbonate by reacting methyl chloroformate with an alcohol (Patent Document 3).

However, the method (v) has a problem that this method can only produce a cyclic carbonate and cannot individually produce various types of carbonate compounds.

The method (vi) has problems that the production facilities are corroded by by-produced hydrogen chloride, phosgene has a high level of toxicity, and the like.

The method (vii) has problems that since it is an equilibrium reaction, a large excess amount of alcohol should be used to increase the yield of a target substance, it is difficult to separate and remove a by-produced asymmetrical carbonate compound (intermediate), and the like.

The method (viii) has a problem that the production facilities are corroded by by-produced hydrogen chloride.

As a method for producing a carbonate compound that solves the above problems, the following method has been proposed.

(ix) A method for producing a carbonate compound and chloroform by reacting hexachloroacetone with an alcohol in the presence of a catalyst (Patent Documents 4 to 6).

CITATION LIST

Patent Literature

Patent Document 1: WO2011/120198
Patent Document 2: JP-A-07-206847
Patent Document 3: JP-A-60-197639
Patent Document 4: U.S. Pat. No. 4,353,831
Patent Document 5: WO2009/072501
Patent Document 6: WO2009/072502

Non-Patent Literature

Non-Patent Document 1: Journal of Catalysis, 2006, Vol. 241, No. 1, pp 34-44

SUMMARY OF THE INVENTION

Problem that the Invention is to Solve

The carbonate compound (carbonate compound composition) obtained by the method (ix) contains a minute amount of chlorine-containing compounds such as hexachloroacetone as a raw material, 1,1,1-trichloroacetic acid ester as an intermediate, and 1,1-dichloroacetic acid ester and 1-chloroacetic acid ester as by-products. The chlorine-containing compounds are hence also contained in minute amounts into diphenyl carbonate obtained from the carbonate compound. In addition, the present inventors confirmed that among the chlorine-containing compounds, 1,1,1-trichloroacetic acid ester, 1,1-dichloro acetic acid ester, and 1-chloroacetic acid ester exert influence (specifically, decrease the reaction rate) on the reaction between diphenyl carbonate and bisphenol A in producing aromatic polycarbonate by the method (ii).

Further, when a carbonate compound is used as a medium of an electrolytic solution of a lithium ion battery, it is preferable to prevent intermixing of the chlorine-containing compound as far as possible.

For the above reason, a carbonate compound having a reduced content of the chlorine-containing compound is required.

The present invention provides a method for producing a carbonate compound that can produce a carbonate compound in which the content of a chlorine-containing compound has been reduced, without using a toxic compound such as phosgene and without by-producing a corrosive gas such as hydrogen chloride; a method for producing diphenyl carbonate that can produce diphenyl carbonate in which the content of a chlorine-containing compound exerting influence on the reaction between diphenyl carbonate and bisphenol A has been reduced, without using a toxic compound such as phosgene and without producing a corrosive gas such as hydrogen chloride; and a method for producing an aromatic polycarbonate that can produce an aromatic polycarbonate with excellent productivity, without using a toxic compound such as phosgene and without producing a corrosive gas such as hydrogen chloride.

Means for Solving the Problem

The method for producing a carbonate compound according to the present invention comprises: a first step of reacting a compound represented by the following Formula (1) with a compound represented by the following Formula (21) or a compound represented by the following Formula (22) to obtain a reaction mixture containing a carbonate compound, and a second step of bringing the reaction mixture containing a carbonate compound into contact with a strongly basic compound.

[Chem. 1]

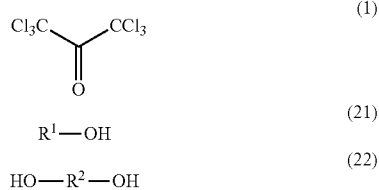

Here, $R^1$ represents a monovalent organic group, and $R^2$ represents a divalent organic group.

It is preferred that the reaction mixture contains a compound represented by the following Formula (41) or a compound represented by the following Formula (42), and in the second step, the reaction mixture is brought into contact with the strongly basic compound to decompose the compound represented by the following Formula (41) or the compound represented by the following Formula (42).

[Chem. 2]

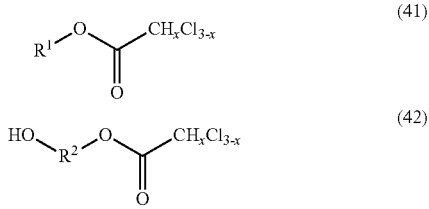

Here, x represents an integer of 0 to 2.

In the method for producing a carbonate compound according to the present invention, it is preferred to obtain a carbonate compound in which a total content of the compounds represented by Formula (41) and the compounds represented by Formula (42) is 5 ppm or less based on the total amount of the carbonate compound.

It is preferred that $R^1$ represents a monovalent aliphatic hydrocarbon group having 1 to 10 carbon atoms and $R^2$ represents a divalent aliphatic hydrocarbon group having 1 to 10 carbon atoms.

In the method for producing a carbonate compound according to the present invention, it is preferred that in the second step, the reaction mixture is brought into contact with the strongly basic compound in the presence of an alcohol.

The strongly basic compound is preferably a salt of a base of which a conjugate acid has a pKa of 11 or higher and an alkali metal ion or an alkaline earth metal ion, and more preferably a hydroxide or an alkoxide of an alkali metal or a hydroxide or an alkoxide of an alkaline earth metal.

In the method for producing a carbonate compound according to the present invention, it is preferred that in the first step, the compound represented by Formula (1) is reacted with the compound represented by Formula (21) or the compounds represented by Formula (22) in the presence of the following catalyst for synthesizing a carbonate compound.

Catalyst for synthesizing a carbonate compound: one or more kinds selected from the group consisting of a weakly basic compound, a phase transfer catalyst, an ion exchange resin, and a compound or oxide of one or more kinds of metals selected from the group consisting of tin, titanium, aluminum, tungsten, molybdenum, zirconium, and zinc.

The method for producing diphenyl carbonate according to the present invention comprises: preparing a carbonate compound by the method for producing a carbonate compound of the present invention, and causing an ester exchange reaction between the obtained carbonate compound and phenol.

The method for producing an aromatic polycarbonate according to the present invention comprises: preparing diphenyl carbonate by the production method of the present invention, and reacting the obtained diphenyl carbonate with a compound represented by the following Formula (6) in the presence of a catalyst for synthesizing a polycarbonate.

[Chem. 3]

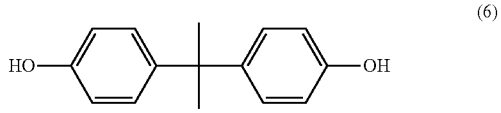

Advantageous Effect of the Invention

According to the method for producing a carbonate compound of the present invention, a carbonate compound in which the content of a chlorine-containing compound has been reduced, can be produced without using a toxic compound such as phosgene and without by-producing a corrosive gas such as hydrogen chloride.

According to the method for producing diphenyl carbonate of the present invention, diphenyl carbonate in which the content of a chlorine-containing compound exerting influence on the reaction between diphenyl carbonate and bisphenol A has been reduced, can be produced without using a toxic compound such as phosgene and without by-producing a corrosive gas such as hydrogen chloride.

According to the method for producing an aromatic polycarbonate of the present invention, an aromatic polycarbonate can be produced with excellent productivity, without using a toxic compound such as phosgene and without producing corrosive gas such as hydrogen chloride.

BRIEF DESCRIPTION OF THE DRAWINGS

FIG. 1 is a graph showing the temporal change in the concentration of butyl dichloroacetate in Examples 35 to 40.

MODE FOR CARRYING OUT THE INVENTION

In the present specification, a compound represented by Formula (1) is described as Compound (1). The compounds represented by other formulae are also described in the same manner.

<Carbonate Compound>

The carbonate compound obtained by the production method of the present invention is a compound having a carbonate bond {—O—C(=O)—O—}.

As the compound having a carbonate bond (hereinafter, also called a carbonate compound), compound (31) or compound (32) is mentioned.

[Chem. 4]

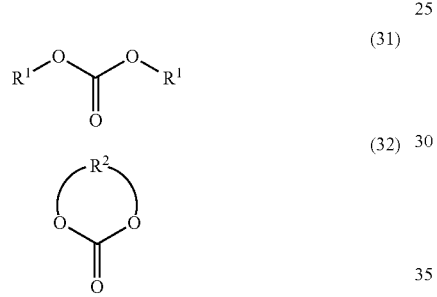

(Compound (31))

$R^1$ represents a monovalent organic group, and preferably represents a monovalent aliphatic hydrocarbon group or a monovalent aromatic hydrocarbon group. As a raw material used in the method for producing diphenyl carbonate that will be described later, a monovalent aliphatic hydrocarbon group is more preferable. $R^1$'s on the left and right side may be the same groups or different groups.

The monovalent aliphatic hydrocarbon group may contain an ethereal oxygen atom. The monovalent aliphatic hydrocarbon group may be linear, branched, or cyclic.

As the monovalent aliphatic hydrocarbon group, monovalent aliphatic hydrocarbon groups having 1 to 10 carbon atoms are preferable. In view of usefulness of Compound (31), methyl group, ethyl group, n-propyl group, i-propyl group, or butyl group is more preferable.

The monovalent aromatic hydrocarbon group may have a substituent of an aliphatic hydrocarbon group or an aromatic hydrocarbon group on the aromatic nucleus.

As the monovalent aromatic hydrocarbon group, monovalent aromatic hydrocarbon groups having 6 to 16 carbon atoms are preferable.

The monovalent aromatic hydrocarbon group includes phenyl group, methylphenyl group, ethylphenyl group, naphthyl group, and the like. Among these, in view of usefulness of Compound (31), phenyl group is preferable.

(Compound (32))

Compound (32) is a cyclic carbonate compound.

$R^2$ represents a divalent organic group and preferably represents a divalent aliphatic hydrocarbon group or a divalent aromatic hydrocarbon group. In view of usefulness of Compound (32), a divalent aliphatic hydrocarbon group is more preferable.

The divalent aliphatic hydrocarbon group may contain an ethereal oxygen atom.

The divalent aliphatic hydrocarbon group may be linear, branched, or cyclic.

As $R^2$, divalent aliphatic hydrocarbon groups having 1 to 10 carbon atoms are preferable. In view of usefulness of Compound (32), —$CH_2CH_2$—, —$CH_2CH(CH_3)$—, or —$CH_2CH_2CH_2$— is more preferable.

Compound (32) include ethylene carbonate, propylene carbonate, 1,3-propylene carbonate, and the like.

<Method for Producing Carbonate Compound>

Compound (31) can be obtained by reacting Compound (1) with Compound (21).

Compound (32) can be obtained by reacting Compound (1) with Compound (22).

[Chem. 5]

The method for producing a carbonate compound of the present invention is a method containing a step of reacting Compound (1) with Compound (21) or Compound (22), to obtain a reaction mixture containing a carbonate compound, and a step of bringing the reaction mixture into contact with a strongly basic compound.

The reaction mixture of the present invention contains at least a target carbonate compound and a by-product not being a target, and may contain an unreacted substance, an intermediate, a solvent, and a catalyst.

The method for producing a carbonate compound of the present invention is specifically a method including the following steps (a) to (d).

(a) A step of reacting Compound (1) with Compound (21) or Compound (22), in the presence of a catalyst for synthesizing a carbonate compound as necessary, to thereby obtain a reaction mixture containing a carbonate compound.

(b) A step of as necessary purifying the reaction mixture obtained in the step (a) to thereby obtain a purified reaction mixture.

(c) A step of bringing the reaction mixture containing a carbonate compound, which is obtained in the step (a) or (b), into contact with a strongly basic compound, in the presence of an alcohol as necessary, to thereby obtain a reacting mixture treated with a strong base.

(d) A step of as necessary recovering a carbonate compound from the reaction mixture obtained in the step (c) to thereby obtain a carbonate compound in which the content of a chlorine-containing compound has been reduced.

(Step (a))

Compound (1):

Compound (1) is hexachloroacetone.

Hexachloroacetone can be produced by the method for chlorinating acetone that is disclosed in JP-B-60-52741 and JP-B-61-16255.

Compound (21):

Compound (21) includes monovalent aliphatic alcohols and monovalent phenols.

As the monovalent aliphatic alcohol, in view of versatility of being used industrially, saturated aliphatic alcohols are preferable, and alkane monols having 1 to 10 carbon atoms are more preferable.

Examples of the alkane monols having 1 to 10 carbon atoms include methanol, ethanol, n-propanol, i-propanol, n-butanol, s-butanol, t-butanol, 1-pentanol, 2-pentanol, 2-methyl-2-butanol, 3-methyl-1-butanol, 2-ethylbutanol, tetrahydrofurfuryl alcohol, neopentyl alcohol, n-octanol, furfuryl alcohol, 3-pentanol, 2-methyl-1-butanol, 3-methyl-2-butanol, 4-methyl-2-pentanol, allyl alcohol, 1-hexanol, cyclohexanol, ethylene glycol monoethyl ether, ethylene glycol monobutyl ether, ethylene glycol monomethyl ether (3-oxa-n-butanol), ethylene glycol monomethoxymethyl ether, ethylene chlorohydrin, diethylene glycol monoethyl ether, diethylene glycol monomethyl ether, propylene glycol monoethyl ether, propylene glycol monomethyl ether, propylene chlorohydrin, and the like.

As the monovalent aliphatic alcohol, in view of usefulness of Compound (31), alkane monols having 1 to 4 carbon atoms are more preferable. Specifically, methanol, ethanol, n-propanol, i-propanol, n-butanol, t-butanol, and 3-oxa-n-butanol are more preferable.

Examples of the monovalent phenols include phenol, ethylphenol, octylphenol, dimethylphenol, orthomethoxyphenol, cresol, hydroxybiphenyl, paracumylphenol, naphthol, and benzylphenol. Among these, in view of usefulness of Ccompound (31), phenol is preferable.

Compound (22):

Compound (22) includes divalent aliphatic alcohols and divalent phenols.

Examples of the divalent aliphatic alcohols include ethylene glycol, diethylene glycol (3-oxa-1,5-pentanediol), triethylene glycol, tetraethylene glycol, dipropylene glycol, tripropylene glycol, 3-chloro-1,2-propanediol, 2-chloro-1,3-propanediol, cyclohexanediol, 1,2-propylene glycol, 1,3-propanediol, 1,2-butanediol, 1,3-butanediol, 1,4-butanediol, 1,4-butenediol, 2-methyl-2,4-pentanediol (hexylene glycol), 3-methyl-1,5-pentanediol, 1,5-pentanediol, and 1,6-hexanediol, in view of versatility of being used industrially.

As the divalent aliphatic alcohols, in view of usefulness of Compound (32), ethylene glycol, 1,2-propylene glycol, 3-methyl-1,5-pentanediol, 1,6-hexanediol, 1,3-propanediol, and 1,4-butanediol are preferable, and 1,2-propylene glycol (HO—$CH_2CH(CH_3)$—OH), ethylene glycol (HO—$CH_2CH_2$—OH), and 3-oxa-1,5-pentanediol (HO—$CH_2CH_2OCH_2CH_2$—OH) are more preferable.

Catalyst for Synthesizing Carbonate Compound:

In view of reactivity between Compound (1) and Compound (21) or Compound (22), it is preferable to use a catalyst for synthesizing a carbonate compound.

As the catalyst for synthesizing a carbonate compound, it is preferable to use one or more kinds selected from the group consisting of basic compounds, phase transfer catalysts, ion exchange resins, and compounds and oxides of one or more kinds of metals selected from the group consisting of tin, titanium, aluminum, tungsten, molybdenum, zirconium, and zinc.

Examples of the basic compound include alkali metal hydroxides, alkaline earth metal hydroxides, alkali metal alkoxides, alkaline earth metal alkoxides, alkali metal salts, and alkaline earth metal salts.

The alkali metal hydroxide includes LiOH, NaOH, KOH, RbOH, and CsOH.

The alkaline earth metal hydroxide includes $Be(OH)_2$, $Ca(OH)_2$, and $Sr(OH)_2$.

The alkali metal alkoxide includes salts of an alkali metal and Compound (21). Specific examples thereof include $LiOCH_3$, $NaOCH_3$, $KOCH_3$, $RbOCH_3$, $CsOCH_3$, $LiOCH_2CH_3$, $NaOCH_2CH_3$, $KOCH_2CH_3$, $RbOCH_2CH_3$, $CsOCH_2CH_3$, $LiOCH_2CH_2CH_3$, $NaOCH_2CH_2CH_3$, $KOCH_2CH_2CH_3$, $RbOCH_2CH_2CH_3$, $CsOCH_2CH_2CH_3$, $LiOCH(CH_3)_2$, $NaOCH(CH_3)_2$, $KOCH(CH_3)_2$, $RbOCH(CH_3)_2$, $CsOCH(CH_3)_2$, $LiOCH_2CH_2CH_2CH_3$, $NaOCH_2CH_2CH_2CH_3$, $KOCH_2CH_2CH_2CH_3$, $RbOCH_2CH_2CH_2CH_3$, $CsOCH_2CH_2CH_2CH_3$, $LiOC(CH_3)_3$, $NaOC(CH_3)_3$, $KOC(CH_3)_3$, $RbOC(CH_3)_3$, $CsOC(CH_3)_3$, $Li(OC_6H_5)$, $Na(OC_6H_5)$, $K(OC_6H_5)$, $Rb(OC_6H_5)$, and $Cs(OC_6H_5)$.

The alkaline earth metal alkoxide include salts of an alkaline earth metal and Compound (21). Specific examples thereof include $Be(OCH_3)_2$, $Ca(OCH_3)_2$, $Sr(OCH_3)_2$, $Be(OCH_2CH_3)_2$, $Ca(OCH_2CH_3)_2$, $Sr(OCH_2CH_3)_2$, $Be(OCH_2CH_2CH_3)_2$, $Ca(OCH_2CH_2CH_3)_2$, $Sr(OCH_2CH_2CH_3)_2$, $Be(OCH(CH_3)_2)_2$, $Ca(OCH(CH_3)_2)_2$, $Sr(OCH(CH_3)_2)_2$, $Be(OCH_2CH_2CH_2CH_3)_2$, $Ca(OCH_2CH_2CH_2CH_3)_2$, $Sr(OCH_2CH_2CH_2CH_3)_2$, $Be(OC(CH_3)_3)_2$, $Ca(OC(CH_3)_3)_2$, $Sr(OC(CH_3)_3)_2$, $Be(OC_6H_5)_2$, $Ca(OC_6H_5)_2$, and $Sr(OC_6H_5)_2$.

The alkali metal salt includes halide salts, carbonates, hydrogen carbonates, and carboxylates. Specific examples thereof include LiF, LiCl, LiBr, NaF, NaCl, NaBr, KF, KCl, KBr, RbF, RbCl, RbBr, CsF, CsCl, CsBr, $Li_2(CO_3)$, $LiHCO_3$, $(CH_3CO_2)Li$, $Na_2(CO_3)$, $NaHCO_3$, $(CH_3CO_2)Na$, $K_2(CO_3)$, $KHCO_3$, $(CH_3CO_2)K$, $Rb_2(CO_3)$, $RbHCO_3$, $(CH_3CO_2)Rb$, $Cs_2(CO_3)$, $CsHCO_3$, and $(CH_3CO_2)Cs$.

The alkaline earth metal salt includes halide salts, carbonates, hydrogen carbonates, and carboxylates. Specific examples thereof include $BeF_2$, $BeCl_2$, $BeBr_2$, $CaF_2$, $CaCl_2$, $CaBr_2$, $SrF_2$, $SrCl_2$, $SrBr_2$, $BeCO_3$, $Be(HCO_3)_2$, $(CH_3CO_2)_2Be$, $CaCO_3$, $Ca(HCO_3)_2$, $(CH_3CO_2)_2Ca$, $SrCO_3$, $Sr(HCO_3)_2$, and $(CH_3CO_2)_2Sr$.

The phase transfer catalyst includes quaternary ammonium salts, quaternary phosphonium salts, quaternary arsonium salts, and sulfonium salts. Specific examples thereof include tetramethylammonium fluoride, tetramethylammonium chloride, tetramethylammonium bromide, tetraethylammonium fluoride, tetraethylammonium chloride, tetraethylammonium bromide, tetra-n-propylammonium fluoride, tetra-n-propylammonium chloride, tetra-n-propylammonium bromide, tetra-n-butylammonium fluoride, tetra-n-butylammonium chloride, tetra-n-butylammonium bromide, tri-n-octylmethylammonium fluoride, tri-n-octylmethylammonium chloride, tri-n-octylmethylammonium bromide, tetraethylphosphonium fluoride, tetraethylphosphonium chloride, tetraethylphosphonium bromide, tetra-n-butylphosphonium fluoride, tetra-n-butylphosphonium chloride, tetra-n-butylphosphonium bromide, tri-n-octylethylphosphonium fluoride, tri-n-octylethylphosphonium chloride, tri-n-octylethylphosphonium bromide, cetyltriethylphosphonium fluoride, cetyltriethylphosphonium chloride, cetyltriethylphosphonium bromide, cetyltri-n-butylphosphonium fluoride, cetyltri-n-butylphosphonium chloride, cetyltri-n-butylphosphonium bromide, n-butyltriphenylphosphonium fluoride, n-butyltriphenylphosphonium chloride, n-butyltriphenylphosphonium bromide, n-amyltriphenylphosphonium fluoride, n-amyltriphenylphosphonium chloride, n-amyltriphenylphosphonium bromide, methyltriphenylphosphonium fluoride, methyltriphenylphosphonium chloride, methyltriphenylphosphonium bromide, benzyltriphenylphosphonium fluoride, benzyltriphenylphosphonium chloride, benzyltriphenylphosphonium bromide, tetraphenylphosphonium fluoride, tetraphenylphosphonium chloride, tetraphenylphosphonium bromide, triphenylmethylarsonium fluoride, tetraphenylarsonium fluoride, triphenylmethylarsonium chloride, tetraphenylarsonium chloride, tetraphenylarsonium bromide, di-n-butylmethylsulfonium iodide, tri-n-butylsulfonium tetrafluoroborate, dihexylmethylsulfonium iodide, dicyclohexylmethylsulfonium iodide, dodecylmethylethylsulfonium chloride, and tris(diethylamino)sulfonium difluorotrimethyl silicate.

The ion exchange resin includes cationic ion exchange resins and anionic ion exchange resins. Examples of commercially available products thereof include Diaion (registered trade mark) series (manufactured by Mitsubishi Chemical Corporation), Amberlite (registered trade mark) series (manufactured by Rohm and Haas Company), and Amberlyst (registered trade mark) series (manufactured by Rohm and Haas Company).

In view of the reaction rate, the ion exchange resin is preferably an anionic ion exchange resin having halogen ions as anions.

Examples of the compounds or oxides of one or more kinds of metals selected from the group consisting of tin, titanium, aluminum, tungsten, molybdenum, zirconium and zinc, include titanium compounds (tetrabutyl titanate, tetrapropyl titanate, tetraethyl titanate, tetramethyl titanate, and the like), organic tin compounds (tin octylate, monobutyltin oxide, monobutyltin tris(2-ethylhexanoate), dibutyltin oxide, dibutyltin laurate, dibutyltin diacetate, monobutyltin hydroxyoxide, and the like), stannous oxide, tin halides (stannous chloride, stannous bromide, stannous iodide, and the like), and aluminum chloride.

As the catalyst for synthesizing a carbonate compound, a basic compound or a phase transfer catalyst is preferable, in view of the reaction activity and selectivity of the target substance and in view of capability of being used industrially at a low cost. Among the basic compounds, strongly basic compounds (alkali metal hydroxides, alkaline earth metal hydroxides, alkali metal alkoxides, and alkaline earth metal alkoxides) exhibit a high degree of reaction activity but, in a carbonate compound synthesis reaction which is performed under relatively severe conditions to increase the yield of a target substance by completing the reaction, they markedly cause a side reaction decomposing the target carbonate compound at the final stage of the reaction, and this leads to the reduction in yield. Accordingly, as the basic compound, a weakly basic compound (alkali metal salts or alkaline earth metal salts) is more preferable. Specifically, a salt of a base of which a conjugate acid has a pKa of less than 11 and an alkali metal ion or alkaline earth metal ion is preferable, and $K_2CO_3$, $Na_2CO_3$, $KHCO_3$, and $NaHCO_3$ are particularly preferable.

Solvent:

Many of Compounds (21) or Compounds (22) have low compatibility with Compound (1). Therefore, at the initial stage, the reaction may be a heterogeneous reaction system in some cases. Accordingly, during the reaction, a solvent may be used to promote the reaction. Here, considering volumetric efficiency of the reactor and loss of the target substance caused at the time of a solvent separating step, it is preferable that the reaction be performed without a solvent as far as possible.

As the solvent, those which stably exist at a reaction temperature and in which the raw materials exhibit high solubility may be used. It is preferable to use a solvent having a boiling point different from that of Compound (1), Compound (21) or Compound (22), and a by-product, in the respect that such a solvent can be separated from these compounds by distillation after the reaction, or to use Compound (21) or Compound (22) as a solvent.

As the solvent, carbonate compounds having different boiling points, Compound (21) or Compound (22), ethers having a relatively high boiling point, and the like are preferable. Specific examples thereof include ethylene carbonate, propylene carbonate, dimethyl carbonate, diethyl carbonate, dipropyl carbonate, dibutyl carbonate, dioctyl carbonate, glyme, diglyme, triglyme, and tetraglyme.

Reaction Conditions:

A ratio between a molar number of Compound (21) and a molar number of Compound (1) (Compound (21)/Compound (1)) is preferably 2 or higher, and more preferably 2.5 or higher, in view of increasing the yield of Compound (31).

A ratio between a molar number of Compound (22) and a molar number of Compound (1) (Compound (22)/Compound (1)) is preferably 1 or higher, and more preferably 1.5 or higher, in view of increasing the yield of Compound (32).

The amount of the catalyst is preferably 0.01 to 30 parts by mass based on 100 parts by mass of Compound (1), and considering the reaction activity and a catalyst removing step after the reaction, it is more preferably 0.1 to 10 parts by mass.

In the method for producing a carbonate compound of the present invention, it is preferable that at least a part of the reaction be performed at a reaction temperature of from 40 to 200° C. If the reaction temperature is lower than 40° C., the yield of a carbonate compound may be extremely reduced in some cases. If the reaction temperature exceeds 200° C., the yield may be reduced markedly in some cases due to the decomposition of Compound (1) used as a raw material and a carbonate compound as a target substance. If the reaction temperature is within the above range, a carbonate compound can be produced with a high yield at a reaction rate that can be industrially realized.

The reaction temperature is preferably from 40 to 160° C., more preferably from 50 to 150° C., and particularly preferably from 60 to 140° C.

As the reaction proceeds, chloroform having a low boiling point is produced. Accordingly, in order to increase the yield of reaction by shifting equilibrium of the reaction to Compound (31) or Compound (32) side and to stoichiometrically complete the reaction, it is preferable to perform the reaction while distilling chloroform, which is produced from the reaction system, away from the reaction system. As the method for distilling away chloroform, the form of reactive distillation utilizing a fact that a boiling point of chloroform is lower than that of Compound (21) or Compound (22) is preferable, in view of the ease of operation.

(Step (b)) Examples of a method for purifying the reaction mixture obtained in the step (a) include a method of recovering a reaction mixture, in which the concentration of a target carbonate compound has been increased due to distillation, from the reaction mixture obtained in the step (a), and the like.

(Step (c))

Chlorine-Containing Compound:

The reaction mixture obtained in the step (a) or step (b) contains the target carbonate compound and a minute amount of chlorine-containing compounds.

As the chlorine-containing compound, Compound (41) or Compound (42) was confirmed. Here, x represents an integer of 0 to 2.

[Chem. 6]

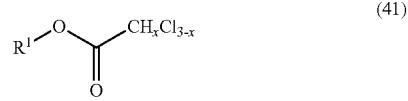
(41)

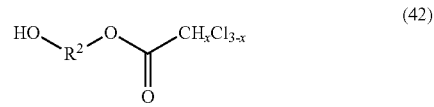
(42)

Compound (41) or Compound (42) is an intermediate in which —CCl₃ at one side of Compound (1) has reacted alone with Compound (21) or Compound (22), or a by-product produced by an interchange reaction between a chlorine atom of the intermediate and a hydrogen atom of hydroxyl group of Compound (21) or Compound (22) during the reaction.

Compound (41) or Compound (42) has been confirmed by the formation of Compound (5) through an ester exchange reaction with phenol, at the time when an ester exchange reaction is caused between a carbonate compound contained in the reaction mixture and phenol so as to obtain diphenyl carbonate used for producing an aromatic polycarbonate.

[Chem. 7]

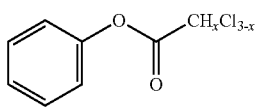

(5)

As described in examples, it was confirmed that Compound (41), Compound (42), and Compound (5) exert influence on the reaction (specifically, decrease the reaction rate) between diphenyl carbonate and bisphenol A in producing an aromatic polycarbonate. As a result of thorough examination on the influence, it was confirmed that the reaction is influenced even if just 50 ppm of Compound (41), Compound (42), and Compound (5) are contained in the carbonate compound. It was also found that depending on the chlorine-containing compound, the reaction is influenced even if the content is just 5 ppm or 1 ppm.

Accordingly, when the carbonate compound produced by the method of reacting Compound (1) with Compound (21) or Compound (22) is used for producing an aromatic polycarbonate, it is important to control the total content of Compound (41) and Compound (42) contained in the carbonate compound to be 50 ppm or less, preferably 5 ppm or less, and more preferably 1 ppm or less.

Strongly Basic Compound:

As a method for reducing the content of a chlorine-containing compound contained in a reaction mixture containing the carbonate compound obtained by reacting Compound (1) with Compound (21) or Compound (22), a method of decomposing and removing by bringing it into contact with a strongly basic compound was found to be excellently effective.

As the strongly basic compound, salts of a base of which a conjugate acid has a pKa of 11 or higher and an alkali metal ion or an alkaline earth metal ion are preferable, and hydroxides or alkoxides of alkali metals or hydroxides or alkoxides of alkaline earth metals are more preferable.

Using salts of a base of which a conjugate acid has a pKa of 11 or higher and an alkali metal ion or an alkaline earth metal ion makes it possible to effectively decompose and remove a chlorine-containing compound. Table 1 shows approximate pKa of the conjugate acids. Incidentally, even when salts of a base of which a conjugate acid has a pKa of less than 11 and an alkali metal ion or an alkaline earth metal ion are used, by optimizing treatment conditions such as increasing the reaction temperature or lengthening the reaction time, a chlorine-containing compound can be decomposed and removed.

TABLE 1

| Base | Conjugate acid | pKa of conjugate acid |
|---|---|---|
| Cl⁻ | HCl | −7 |
| HCO₃⁻ | H₂CO₃ | 3.7 |
| CH₃CO₂⁻ | CH₃CO₂H | 4.75 |
| C₆H₅O⁻ | C₆H₅OH | 9.9 |
| CO₃²⁻ | HCO₃⁻ | 10.2 |
| (C₂H₅)₂NH | (C₂H₅)₂NH₂⁺ | 10.7 |
| (C₂H₅)₃N | (C₂H₅)₃NH⁺ | 10.7 |
| HO⁻ | H₂O | 15.7 |
| CH₃CH₂O⁻ | CH₃CH₂OH | 16 |
| CH₃CH₂CH₂CH₂O⁻ | CH₃CH₂CH₂CH₂OH | 16 |
| (CH₃)₃CO⁻ | (CH₃)₃COH | 18 |

The alkali metal hydroxide includes LiOH, NaOH, KOH, RbOH, and CsOH.

The alkaline earth metal hydroxide includes Be(OH)₂, Ca(OH)₂, and Sr(OH)₂.

The alkali metal alkoxide includes salts of an alkali metal and Compound (21). Specific examples thereof include LiOCH₃, NaOCH₃, KOCH₃, RbOCH₃, CsOCH₃, LiOCH₂CH₃, NaOCH₂CH₃, KOCH₂CH₃, RbOCH₂CH₃, CsOCH₂CH₃, LiOCH₂CH₂CH₃, NaOCH₂CH₂CH₃, KOCH₂CH₂CH₃, RbOCH₂CH₂CH₃, CsOCH₂CH₂CH₃, LiOCH(CH₃)₂, NaOCH(CH₃)₂, KOCH(CH₃)₂, RbOCH(CH₃)₂, CsOCH(CH₃)₂, LiOCH₂CH₂CH₂CH₃, NaOCH₂CH₂CH₂CH₃, KOCH₂CH₂CH₂CH₃, RbOCH₂CH₂CH₂CH₃, CsOCH₂CH₂CH₂CH₃, LiOC(CH₃)₃, NaOC(CH₃)₃, KOC(CH₃)₃, RbOC(CH₃)₃, CsOC(CH₃)₃, Li(OC₆H₅), Na(OC₆H₅), K(OC₆H₅), Rb(OC₆H₅), and Cs(OC₆H₅).

The alkaline earth metal alkoxide include salts of an alkaline earth metal and Compound (21). Specific examples thereof include Be(OCH₃)₂, Ca(OCH₃)₂, Sr(OCH₃)₂, Be(OCH₂CH₃)₂, Ca(OCH₂CH₃)₂, Sr(OCH₂CH₃)₂, Be(OCH₂CH₂CH₃)₂, Ca(OCH₂CH₂CH₃)₂, Sr(OCH₂CH₂CH₃)₂, Be(OCH(CH₃)₂)₂, Ca(OCH(CH₃)₂)₂, Sr(OCH(CH₃)₂)₂, Be(OCH₂CH₂CH₂CH₃)₂, Ca(OCH₂CH₂CH₂CH₃)₂, Sr(OCH₂CH₂CH₂CH₃)₂, Be(OC(CH₃)₃)₂, Ca(OC(CH₃)₃)₂, Sr(OC(CH₃)₃)₂, Be(OC₆H₅)₂, Ca(OC₆H₅)₂, and Sr(OC₆H₅)₂.

Treatment Method:

When a hydroxide of an alkali metal or alkaline earth metal is used, it is preferable to use its aqueous solution. In many cases, a reaction mixture containing a carbonate compound is not uniformly mixed with the aqueous solution of a hydroxide of an alkali metal or alkaline earth metal. Therefore, it is preferable to employ a form of mixing that may reduce the diameter of liquid droplets at the time of mixing. Moreover, when an alkoxide of an alkali metal or alkaline earth metal is used, it is preferable to use its alcohol solution. In some cases, the alcohol solution becomes a uniform solution with a reaction mixture containing a carbonate compound. However, since an alkoxide of an alkali metal or alkaline earth metal is precipitated in some cases, the form of mixing such as stirring is important. Whether a non-uniform system in which an alkoxide of an alkali metal or alkaline earth metal is precipitated is formed or a uniform system in which it has dissolved is formed will depend on the concentration of alcohol and a mass ratio between a carbonate compound and the alcohol solution.

When an aqueous solution of a hydroxide of an alkali metal or alkaline earth metal is used, the concentration of the hydroxide is preferably 1 to 50% by mass, and more preferably 5 to 30% by mass. If the concentration of the hydroxide is too low, sometimes the treatment time is excessively lengthened. If the concentration of the hydroxide is too high, sometimes the carbonate compound is decomposed.

The amount of the hydroxide of an alkali metal or alkaline earth metal is preferably an amount sufficient relative to a chlorine-containing compound in the reaction mixture, and is more preferably 1 to 100 parts by mass based on 100 parts by mass of the carbonate compound. If the amount of the hydroxide is too small, it is difficult to obtain a sufficient removal rate. If the amount of the hydroxide is too large, sometimes the content of useless hydroxide not dissolving in the aqueous solution increases or the carbonate compound is decomposed.

The treatment temperature in the case of using the aqueous solution of a hydroxide of an alkali metal or alkaline earth metal varies depending on the strength of a base, the concentration of the hydroxide, and the amount of the aqueous solution, and is preferably 0 to 150° C., and more preferably 20 to 120° C. If the treatment temperature is too low, sometimes the treatment time is excessively lengthened. If the treatment temperature is too high, sometimes the carbonate compound is decomposed.

When an alkoxide of an alkali metal or alkaline earth metal is used, it is preferable to use an alkoxide of the same alcohol as Compound (21) or Compound (22) which is a raw material of the carbonate compound. This is because an ester exchange reaction is caused between the carbonate compound and the alkoxide depending on treatment conditions. Use of an alkoxide of an alcohol different from the raw material of the carbonate compound leads to the loss of a target carbonate compound. For the same reason, it is preferable for the alkoxide to be used as a solution of the same alcohol as Compound (21) or Compound (22) which is a raw material of the carbonate compound.

Examples of a method for preparing an alcohol solution of an alkoxide of an alkali metal or alkaline earth metal include a method of directly reacting an alkali metal or an alkaline earth metal with alcohol; a method of reacting a hydroxide of an alkali metal or alkaline earth metal with alcohol; and a method, which is used for preparing an alkoxide of alcohol having a boiling point higher than that of water or alcohol forming an azeotropic composition with water, of adding an alcohol in a large excess amount to an aqueous solution of a hydroxide of an alkali metal or alkaline earth metal and then increasing the temperature to the boiling point of water or to an azeotropic point of water and alcohol so as to distill away water or the azeotropic composition of water until the existing moisture is completely removed.

When the alcohol solution of an alkoxide of an alkali metal or alkaline earth metal is used, the concentration of alkoxide is preferably 1 to 40% by mass, and more preferably 2 to 20% by mass. If the concentration of alkoxide is too low, sometimes the treatment time is excessively lengthened. If the concentration of alkoxide is too high, sometimes the carbonate compound is decomposed. Moreover, in some cases, solubility decreases when the alkoxide is mixed with the carbonate compound, and the alkoxide is precipitated, whereby the treatment time is excessively lengthened.

The amount of an alkoxide of an alkali metal or alkaline earth metal is preferably an amount sufficient relative to a chlorine-containing compound in the reaction mixture, and is more preferably 1 to 100 parts by mass based on 100 parts by mass of the carbonate compound. If the amount of alkoxide is too small, it is difficult to obtain a sufficient removal rate. If the amount of alkoxide is too large, sometimes the amount of a by-product such as dialkyl ether produced by the reaction between the carbonate compound and the alkoxide increases.

The treatment temperature in the case of using the alcohol solution of an alkoxide of an alkali metal or alkaline earth metal varies depending on the amount of the alkoxide solution and the concentration of the alkoxide, and is preferably 0 to 150° C., and more preferably 20 to 120° C. If the treatment temperature is too low, sometimes the treatment time is excessively lengthened. If the treatment temperature is too high, sometimes the carbonate compound is decomposed.

In the method for producing a carbonate compound of the present invention, it is preferable to bring the reaction mixture into contact with a strongly basic compound in the presence of an alcohol. If an alcohol is present in the system, solubility of the strongly basic compound is improved, and the decomposition of a chlorine-containing compound can be promoted.

(Step (d))

The method of recovering a high-purity carbonate compound from the reaction mixture obtained in the step (c) includes a method of recovering a carbonate compound by distillation. Incidentally, since many of the carbonate compounds to be recovered have a high boiling point, if distillation is performed in the presence of the strongly basic compound used in the step (c), sometimes decomposition of the carbonate compound proceeds. Accordingly, it is preferable to separate and remove the strongly basic compound from the reaction mixture, before distillation for recovering a high-purity carbonate compound is performed.

When an aqueous solution of a hydroxide of an alkali metal or alkaline earth metal is used, phase separation is performed after the step (c) so as to separate and remove a water phase, whereby the hydroxide can be separated and removed. When an aqueous solution containing the hydroxide at a high concentration is used as the aqueous solution, the phase of the carbonate compound is washed with pure water after phase separation, whereby the residual hydroxide can be sufficiently removed.

When the alcohol solution of an alkoxide of an alkali metal or alkaline earth metal is used, and the alcohol has a low boiling point, a method is exemplified in which the alcohol is distilled away by distillation, and then the precipitated alkoxide is separated and removed by filtration. As another method, a method is exemplified in which water is added to the reaction mixture to extract the alkoxide to the water side, and then a water phase is separated and removed by phase separation. The latter method is industrially useful since it makes it possible to recover a carbonate compound phase by converting surplus alkoxide into alcohol.

(Operation and Effect)

In the method for producing a carbonate compound of the present invention described so far, since a carbonate compound is obtained by reacting Compound (1) with Compound (21) or Compound (22), it is possible to produce a carbonate compound without using a toxic compound such as phosgene and without by-producing corrosive gas such as hydrogen chloride. Moreover, since a reaction mixture containing the obtained carbonate compound is brought into contact with a strongly basic compound, it is possible to produce a carbonate compound in which the content of a chlorine-containing compound has been reduced.

<Method for Producing Diphenyl Carbonate>

The method for producing diphenyl carbonate of the present invention is a method of causing an ester exchange reaction between the carbonate compound obtained by the method for producing a carbonate compound of the present invention and phenol. The ester exchange reaction can be performed by the methods disclosed in JP-A-10-036321, JP-A-2007-254311, and the like. As a method for recovering high-purity diphenyl carbonate from the reaction mixture obtained by the ester exchange reaction, a method for recovering diphenyl carbonate by distillation is exemplified.

(Operation and Effect)

In the method for producing diphenyl carbonate of the present invention described so far, since the carbonate compound obtained by the method for producing a carbonate compound of the present invention is used, it is possible to produce diphenyl carbonate in which the content of chlorine-containing compounds exerting influence on the reaction between diphenyl carbonate and bisphenol A has been reduced, without using a toxic compound such as phosgene and by-producing corrosive gas such as hydrogen chloride.

Incidentally, when diphenyl carbonate is directly obtained by reacting Compound (1) with phenol according to the method for producing a carbonate compound of the present invention, since the rate of the reaction between Compound (1) and phenol is extremely slow, a large amount of 1,1,1-trichloroacetic acid phenyl ester as an intermediate is by-produced and this makes it difficult to remove a chlorine-containing compound. However, if Compound (1) is reacted with an aliphatic alcohol according to the method for producing a carbonate compound of the present invention to obtain an aliphatic carbonate first, and then an ester exchange reaction is caused between the aliphatic carbonate and phenol to obtain diphenyl carbonate, the above problem can be solved.

<Method for Producing an Aromatic Polycarbonate>

The method for producing an aromatic polycarbonate of the present invention is a method of reacting diphenyl carbonate obtained by the method for producing diphenyl carbonate of the present invention with Compound (6) in the presence of a catalyst for synthesizing polycarbonate.

[Chem. 8]

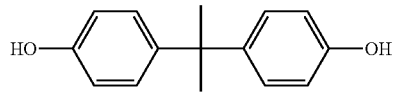

(6)

As a method for producing aromatic polycarbonate by reacting diphenyl carbonate with bisphenol A, the method disclosed in Patent Document 1 and the like are exemplified.

As the catalyst for synthesizing polycarbonate, the catalyst disclosed in Patent Document 1 and the like are exemplified.

(Operation and Effect)

The method for producing an aromatic polycarbonate of the present invention described above is a method of reacting diphenyl carbonate with Compound (6) in the presence of the catalyst for synthesizing polycarbonate. Accordingly, it is possible to produce an aromatic polycarbonate without using a toxic compound such as phosgene and without by-producing corrosive gas such as hydrogen chloride. In addition, since the diphenyl carbonate which is obtained by the method for producing diphenyl carbonate of the present invention and in which the content of a chlorine-containing compound has been reduced is used, it is possible to inhibit a chlorine-containing compound from exerting influence on the reaction between diphenyl carbonate and bisphenol A, and to produce an aromatic polycarbonate with excellent productivity.

EXAMPLES

Hereinafter, the present invention will be described in more detail based on examples, but the present invention is not limited to the examples.

Examples 3 to 8 are synthesis examples, Examples 9 to 31 and 35 to 40 are experimental examples, Examples 32 to 34, 41, and 42 are invention examples, and Examples 1 and 2 are comparative examples.

(Gas Chromatography)

For performing analysis by gas chromatography (hereinafter, described as GC), 6890 series manufactured by Agilent was used. The analysis conditions were as follows.

Column: DB-1301 (manufactured by J&W Scientific), 60 m

Inner diameter: 0.25 mm

Film thickness: 1 μm

Column temperature: 40° C. (rate of temperature increase of 10° C./min), 280° C.

Injection temperature: 300° C.

Detector temperature: 300° C.

Detection method: FID

Example 1

Synthesis of Dibutyl Carbonate

Step (a)

In a three-neck glass-made reactor having internal volume of 10 L in which a dropping funnel and a distillation line having a cooling portion cooled to 10° C. were installed were charged 50 g of $K_2CO_3$ (reagent manufactured by Tokyo Chemical Industry Co., Ltd., P1748) and 3408 g (46.0 mol) of 1-butanol (reagent manufactured by Tokyo Chemical Industry Co., Ltd., B0704). After warming at 30° C. by an oil bath, the whole amount of 4154 g (15.7 mol) of hexachloroacetone (reagent manufactured by Tokyo Chemical Industry Co., Ltd., H0335) was added dropwise thereto from the dropping funnel under stirring, while adjusting a dropping rate such that the temperature in the reactor did not exceed 50° C., whereby the whole reagent was added dropwise. After the dropwise addition ended, the temperature of the oil bath was slowly increased up to 100° C. over 2 hours under sufficient stirring. Chloroform generated by the reaction during temperature increase was recovered as liquid from the distillation line installed in the reactor. From the point in time when the temperature of the oil bath reached 100° C., the internal pressure of the system was slowly reduced by using a vacuum pump through a pressure-regulating valve installed in the distillation line, and the pressure was continuously reduced until the pressure finally became 20 mmHg. The surplus 1-butanol and dibutyl carbonate in the reactor produced by the reaction were extracted from the distillation line, and distillation was continuously performed until no liquid existed in the reactor finally, thereby recovering the whole reaction mixture (7486 g, recovery rate of 99%).

Step (b)

The reaction mixture was charged in a distillation column having a theoretical stage number of 20, and while adjusting the pressure such that the internal temperature of the distillation still did not become 120° C. or a higher, distillation was performed under reduced pressure. As a result of distillation, 2614 g (yield of 95.5%) of a reaction mixture containing dibutyl carbonate (hereinafter, abbreviated to DBC) having GC purity of 99.8% was recovered. The structure of minute impurities contained in the recovered reaction mixture was analyzed by GC-MASS (gas chromatography-mass spectrometry), and as a result, the existence of chlorine-containing compounds shown in Table 2 was confirmed.

TABLE 2

| Chemical structure | Content (GC area ratio vs DBC) |
|---|---|
| CCl$_3$C(=O)OCH$_2$CH$_2$CH$_2$CH$_3$ | 5 ppm |
| CHCl$_2$C(=O)OCH$_2$CH$_2$CH$_2$CH$_3$ | 2000 ppm |
| CH$_2$ClC(=O)OCH$_2$CH$_2$CH$_2$CH$_3$ | 1 ppm |

Example 2

Synthesis of Diphenyl Carbonate

In accordance with the method disclosed in JP-A-2006-335739, vanadium phenoxide was synthesized by using vanadium oxide as a starting material.

By using vanadium phenoxide as a catalyst, an ester exchange reaction and a disproportionation reaction were performed on the dibutyl carbonate synthesized in Example 1 in accordance with a known method, thereby synthesizing diphenyl carbonate (hereinafter, abbreviated to DPC). By distillation, DPC having GC purity of 99.5% was recovered. The structure of minute impurities contained in the recovered DPC was analyzed by GC-MASS, and as a result, the existence of chlorine-containing compounds shown in Table 3 was newly confirmed.

TABLE 3

| Chemical structure | Content (GC area ratio vs DPC) |
|---|---|
| CCl$_3$C(=O)OC$_6$H$_5$ | 3 ppm |
| CHCl$_2$C(=O)OC$_6$H$_5$ | 1500 ppm |
| CH$_2$ClC(=O)OC$_6$H$_5$ | 1 ppm |

Example 3

Synthesis of Trichloroacetic Acid Butyl Ester

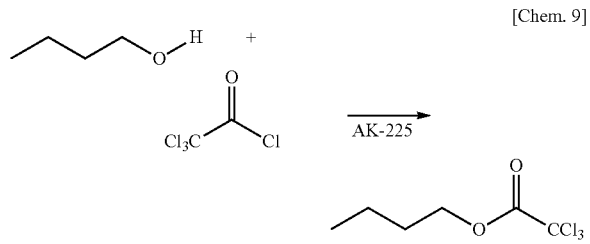

[Chem. 9]

In a 3000 mL glass-made reactor equipped with a stirrer, a reflux condenser at 20° C. and a dropping funnel were charged 1000 g (5.50 mol) of trichloroacetyl chloride (reagent manufactured by Tokyo Chemical Industry Co., Ltd., T0373) and 1000 g of AK-225 (manufactured by ASAHI GLASS CO., LTD), followed by heating to 60° C. with stirring. Subsequently, 448.40 g (6.05 mol) of 1-butanol (reagent manufactured by Tokyo Chemical Industry Co., Ltd., B0704) was added dropwise thereto while adjusting the rate with checking the increase in internal temperature (ΔT) and the generation of hydrogen chloride gas. After the dropwise addition ended, the resultant was heated for 9 hours at 80° C. After the reaction ended, the crude liquid was cooled to room temperature, and then a portion of the crude liquid was collected to analyze its composition by GC-MASS. As a result, it was confirmed that trichloroacetic acid butyl ester (hereinafter, abbreviated to TCAB) was generated as a main product (trichloroacetyl chloride base yield of 96.91%). Thereafter, it was subjected to an alkali washing and water washing and then distilled, thereby obtaining 1109 g (5.05 mol) of a fraction having a GC purity of 99% or higher. For TCAB as a product, structural assignment was conducted by GC-MASS. MASS fragments of TCAB are shown below.

TCAB: MS m/z: 57 (CH$_3$CH$_2$CH$_2$CH$_2$); 117, 119 (CCl$_3$); 183 (CCl$_2$C(=O)OCH$_2$CH$_2$CH$_2$CH$_3$)

Example 4

Synthesis of Dichloroacetic Acid Butyl Ester

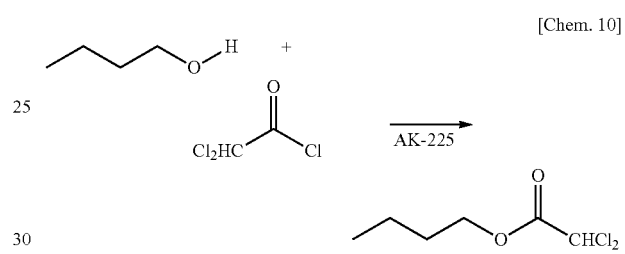

[Chem. 10]

In a 3000 mL glass-made reactor equipped with a stirrer, a reflux condenser at 20° C., and a dropping funnel were charged 811 g (5.50 mol) of dichloroacetyl chloride (reagent manufactured by Tokyo Chemical Industry Co., Ltd., D0313) and 1000 g of AK-225 (manufactured by ASAHI GLASS CO., LTD), followed by heating to 60° C. with stirring. Subsequently, 448.40 g (6.05 mol) of 1-butanol (reagent manufactured by Tokyo Chemical Industry Co., Ltd., B0704) was added dropwise thereto while adjusting the rate with checking the increase in internal temperature (ΔT) and the generation of hydrogen chloride gas. After the dropwise addition ended, the resultant was heated for 9 hours at 80° C. After the reaction ended, the crude liquid was cooled to room temperature, and then a portion of the crude liquid was collected to analyze its composition by GC-MASS. As a result, it was confirmed that dichloroacetic acid butyl ester (hereinafter, abbreviated to DCAB) was generated as a main product (dichloroacetyl chloride base yield of 96.00%). Thereafter, it was subjected to an alkali washing and water washing and then distilled, thereby obtaining 916 g (4.95 mol) of a fraction having a GC purity of 99% or higher. For DCAB as a product, structural assignment was conducted by GC-MASS. MASS fragments of DCAB are shown below.

DCAB: MS m/z: 57 (CH$_3$CH$_2$CH$_2$CH$_2$); 83, 85 (CHCl$_2$); 149 (CHClC(=O)OCH$_2$CH$_2$CH$_2$CH$_3$)

Example 5

Synthesis of Monochloroacetic Acid Butyl Ester

[Chem. 11]

-continued

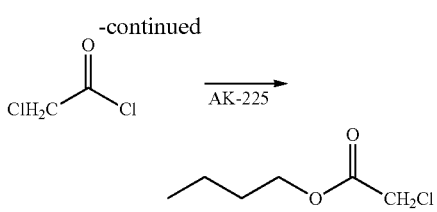

In a 3000 mL glass-made reactor equipped with a stirrer, a reflux condenser at 20° C. and a dropping funnel were charged 621 g (5.50 mol) of monochloroacetyl chloride (reagent manufactured by Tokyo Chemical Industry Co., Ltd., C0098) and 1000 g of AK-225 (manufactured by ASAHI GLASS CO., LTD), followed by heating to 60° C. with stirring. Subsequently, 448.40 g (6.05 mol) of 1-butanol (reagent manufactured by Tokyo Chemical Industry Co., Ltd., B0704) was added dropwise thereto while adjusting the rate with checking the increase in internal temperature (ΔT) and the generation of hydrogen chloride gas. After the dropwise addition ended, the resultant was heated for 9 hours at 80° C. After the reaction ended, the crude liquid was cooled to room temperature, and then a portion of the crude liquid was collected to analyze its composition by GC-MASS. As a result, it was confirmed that mono chloroacetic acid butyl ester (hereinafter, abbreviated to MCAB) was generated as a main product (monochloroacetyl chloride base yield of 98.00%). Thereafter, it was subjected to an alkali washing and water washing and then distilled, thereby obtaining 768 g (5.10 mol) of a fraction having a GC purity of 99% or higher. For MCAB as a product, structural assignment was conducted by GC-MASS. MASS fragments of MCAB are shown below.

MCAB: MS m/z: 57 ($CH_3CH_2CH_2CH_2$); 49, 51 ($CH_2Cl$); 115 ($CH_2C(=O)OCH_2CH_2CH_2CH_3$)

Example 6

Synthesis of Trichloroacetic Acid Phenyl Ester

[Chem. 12]

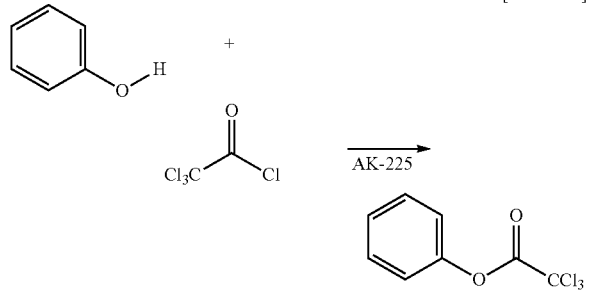

In a 3000 mL glass-made reactor equipped with a stirrer, a reflux condenser at 20° C. and a dropping funnel were charged 1000 g (5.50 mol) of trichloroacetyl chloride (reagent manufactured by Tokyo Chemical Industry Co., Ltd., T0373) and 1000 g of AK-225 (manufactured by ASAHI GLASS CO., LTD), followed by heating to 60° C. with stirring. Subsequently, 569.4 g (6.05 mol) of phenol (reagent manufactured by Tokyo Chemical Industry Co., Ltd., P1610) was liquefied by being warmed at 50° C., and then was added dropwise thereto while adjusting the rate with checking the increase in internal temperature (ΔT) and the generation of hydrogen chloride gas. After the dropwise addition ended, the resultant was heated for 9 hours at 80° C. After the reaction ended, the crude liquid was cooled to room temperature, and then a portion of the crude liquid was collected to analyze its composition by GC-MASS. As a result, it was confirmed that trichloroacetic acid phenyl ester (hereinafter, abbreviated to TCAP) was generated as a main product (trichloroacetyl chloride base yield of 95.91%). Thereafter, it was subjected to an alkali washing and water washing and then distilled, thereby obtaining 1198 g (5.00 mol) of a fraction having a GC purity of 99% or higher. For TCAP as a product, structural assignment was conducted by GC-MASS. MASS fragments of TCAP are shown below.

TCAP: MS m/z: 77 ($C_6H_5$); 117, 119 ($CCl_3$); 203 ($CCl_2C(=O)OC_6H_5$)

Example 7

Synthesis of Dichloroacetic Acid Phenyl Ester

[Chem. 13]

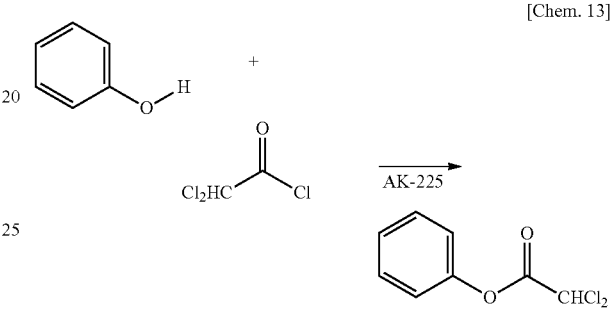

In a 3000 mL glass-made reactor equipped with a stirrer, a reflux condenser at 20° C. and a dropping funnel were charged 811 g (5.50 mol) of dichloroacetyl chloride (reagent manufactured by Tokyo Chemical Industry Co., Ltd., D0313) and 1000 g of AK-225 (manufactured by ASAHI GLASS CO., LTD), followed by heating to 60° C. with stirring. Subsequently, 569.4 g (6.05 mol) of phenol (reagent manufactured by Tokyo Chemical Industry Co., Ltd., P1610) was liquefied by being warmed at 50° C., and then was added dropwise thereto while adjusting the rate with checking the increase in internal temperature (ΔT) and the generation of hydrogen chloride gas. After the dropwise addition ended, the resultant was heated for 9 hours at 80° C. After the reaction ended, the crude liquid was cooled to room temperature, and then a portion of the crude liquid was collected to analyze its composition by GC-MASS. As a result it was confirmed that dichloroacetic acid phenyl ester (hereinafter, abbreviated to DCAP) was generated as a main product (dichloroacetyl chloride base yield of 95.00%). Thereafter, it was subjected to an alkali washing and water washing and then distilled, thereby obtaining 1035 g (5.05 mol) of a fraction having a GC purity of 99% or higher. For DCAP as a product, structural assignment was conducted by GC-MASS. MASS fragments of DCAP are shown below.

DCAP: MS m/z: 77 ($C_6H_5$); 83, 85 ($CHCl_2$); 169 (CHClC(=O)$OC_6H_5$)

Example 8

Synthesis of Monochloroacetic Acid Phenyl Ester

[Chem. 14]

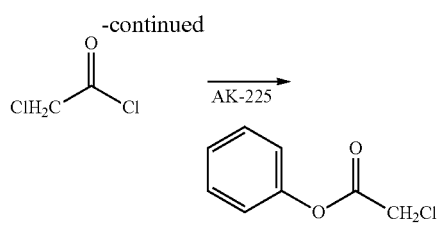

In a 3000 mL glass-made reactor equipped with a stirrer, a reflux condenser at 20° C. and a dropping funnel were charged 621 g (5.50 mol) of monochloroacetyl chloride (reagent manufactured by Tokyo Chemical Industry Co., Ltd., C0098) and 1000 g of AK-225 (manufactured by ASAHI GLASS CO., LTD), followed by heating to 60° C. with stirring. Subsequently, 569.4 g (6.05 mol) of phenol (reagent manufactured by Tokyo Chemical Industry Co., Ltd., P1610) was liquefied by being warmed at 50° C., and then was added dropwise thereto while adjusting the rate with checking the increase in internal temperature (ΔT) and the generation of hydrogen chloride gas. After the dropwise addition ended, the resultant was heated for 9 hours at 80° C. After the reaction ended, the crude liquid was cooled to room temperature, and then a portion of the crude liquid was collected to analyze its composition by GC-MASS. As a result, it was confirmed that monochloroacetic acid phenyl ester (hereinafter, abbreviated to MCAP) was generated as a main product (monochloroacetyl chloride base yield of 96.00%). Thereafter, it was subjected to an alkali washing and water washing and then distilled, thereby obtaining 870 g (5.10 mol) of a fraction having a GC purity of 99% or higher. For MCAP as a product, structural assignment was conducted by GC-MASS. MASS fragments of MCAP are shown below.

MCAP: MS m/z: 77 ($C_6H_5$); 49, 51 ($CH_2Cl$); 135 ($CH_2C(=O)OC_6H_5$)

Examples 9 to 26

Chlorine-Containing Compound Addition Test

By using DPC (polycarbonate resin grade), bisphenol A (hereinafter, abbreviated to BPA), and the chlorine-containing compounds synthesized in Examples 3 to 8, the influence of the chlorine-containing compound on a reaction between DPC and BPA was examined according to the following method.

Into a test tube having internal volume of 5 mL were charged 300 mg (0.0014 mol) of DPC, 319 mg (0.0014 mol) of BPA, and $NaHCO_3$ in an amount of 5 μmol based on 1 mol of BPA, and then the chlorine-containing compounds synthesized separately were added thereto at the concentration shown in Table 4 based on DPC. The internal pressure of the test tube was reduced by using a rotary pump, thereby drying for 1 hour, and the atmosphere was purged with nitrogen gas, followed by heating at 180° C. in a sealed state. The reaction was allowed to proceed while analyzing the DPC concentration in the system over time by GC and comparing to the case to which the chlorine-containing compound was not added. The influence of the chlorine-containing compound on the reaction was evaluated, and the results are summarized in Table 4. The evaluation was made based on a residual ratio of DPC remaining after heating was performed for 20 minutes at 180° C. A numerical value that is higher than a residual ratio of the result (Example 9) of no chlorine-containing compound addition indicates that the reaction rate is influenced.

TABLE 4

| Example | Chlorine-containing compound | Added amount (ppm vs DPC) | Residual ratio of DPC after 20 minutes (%) |
|---|---|---|---|
| 9 | None | — | 40 |
| 10 | MCAP | 5 | 40 |
| 11 | DCAB | 5 | 45 |
| 12 | TCAB | 5 | 45 |
| 13 | MCAP | 5 | 41 |
| 14 | DCAP | 5 | 60 |
| 15 | TCAP | 5 | 41 |
| 16 | DCAB | 50 | 50 |
| 17 | TCAB | 50 | 50 |
| 18 | MCAP | 50 | 50 |
| 19 | DCAP | 50 | 92 |
| 20 | TCAP | 50 | 55 |
| 21 | MCAB | 500 | 45 |
| 22 | DCAB | 500 | 80 |
| 23 | TCAB | 500 | 60 |
| 24 | MCAP | 500 | 80 |
| 25 | DCAP | 500 | 90 |
| 26 | TCAP | 500 | 80 |

Examples 27 to 31

Chlorine-Containing Compound Addition Test

The test was performed in the same manner as in Examples 9 to 26, except that $NaHCO_3$ used as a catalyst was used in an amount of 1 μmol based on 1 mol of BPA. The influence of the chlorine-containing compound on the reaction was evaluated, and the results are summarized in Table 5. The evaluation was made based on a residual ratio of DPC remaining after heating was performed for 20 minutes at 180° C. A numerical value that is higher than a residual ratio of a result (Example 27) of no chlorine-containing compound addition indicates that the reaction rate is influenced.

TABLE 5

| Example | Chlorine-containing compound | Added amount (ppm vs DPC) | Residual ratio of DPC after 20 minutes (%) |
|---|---|---|---|
| 27 | None | — | 50 |
| 28 | DCAB | 1 | 51 |
| 29 | TCAB | 1 | 70 |
| 30 | DCAP | 1 | 55 |
| 31 | TCAP | 1 | 65 |

Example 32

Step (c)

In a Pyrex (registered trademark)-made three-neck flask having internal volume of 200 ml in which a stirrer and a Dimroth condenser (cooled at 10° C.) were installed were charged 100 g of the reaction mixture containing DBC obtained in Example 1 and 5 g of a 25% by mass aqueous NaOH solution, followed by heating to the internal temperature of 80° C. with stirring. After the internal temperature reached 80° C., stirring was performed for 10 hours.

Step (d)

After the stirring ended, the resultant was cooled to room temperature, and the recovered organic phase (DBC) was analyzed by GC. As a result, it was confirmed that the chlorine-containing compound had been decomposed and removed to an extent equal to or lower than the lower limit of detection (1 ppm or less), as shown in Table 6.

TABLE 6

| | Content(GC area ratio vs DBC) | |
|---|---|---|
| Chemical structure | Before treatment | After treatment |
| $CCl_3C(=O)OCH_2CH_2CH_2CH_3$ | 5 ppm | <1 ppm |
| $CHCl_2C(=O)OCH_2CH_2CH_2CH_3$ | 2000 ppm | <1 ppm |
| $CH_2ClC(=O)OCH_2CH_2CH_2CH_3$ | 1 ppm | <1 ppm |

Example 33

Step (c)

A reaction mixture containing DBC was treated in the same manner as in Example 32, except that 5 g of a 25% by mass aqueous KOH solution was used, and the treatment was performed for 10 hours at room temperature (20° C.).

Step (d)

After the stirring ended, the resultant was cooled to room temperature, and DBC was recovered. The recovered DBC was analyzed by GC. As a result, it was confirmed that the chlorine-containing compound had been decomposed and removed to an extent equal to or lower than the lower limit of detection (1 ppm or less), as shown in Table 7.

TABLE 7

| | Content (GC area ratio vs DBC) | |
|---|---|---|
| Chemical structure | Before treatment | After treatment |
| $CCl_3C(=O)OCH_2CH_2CH_2CH_3$ | 5 ppm | <1 ppm |
| $CHCl_2C(=O)OCH_2CH_2CH_2CH_3$ | 2000 ppm | <1 ppm |
| $CH_2ClC(=O)OCH_2CH_2CH_2CH_3$ | 1 ppm | <1 ppm |

Example 34

Steps (a) and (b)

In the same manner as in Example 1, 6000 g of a reaction mixture containing DBC was obtained.

Step (c)

In a distillation column equipped with a Pyrex (registered trademark)-made still having internal volume of 3 L were charged 2600 g of 1-butanol and 203 g of a 48% by mass aqueous KOH solution, followed by heating and extracting azeotropic composition of 1-butanol and water as a fraction, thereby removing water in the still. In accordance with Karl Fischer's method, the amount of moisture was determined, and it was confirmed that the amount of moisture in the still was 1000 ppm or less. Subsequently, after cooling to room temperature, 2000 g of a 1-butanol solution containing $KOCH_2CH_2CH_2CH_3$ (hereinafter, abbreviated to n-BuOK) was recovered from the distillation still.

In a 10 L Pyrex (registered trademark)-made three-neck flask in which a Dimroth condenser cooled to 20° C. was installed were charged 2000 g of the 1-butanol solution containing n-BuOK and 6000 g of a reaction mixture containing DBC. The entire flask was placed in an oil bath, and the temperature of the oil bath was increased to 120° C. under stirring. After the temperature of the oil bath was increased to 120° C., stirring was continued for 1 hour, and then the treatment ended. After the treatment, the flask was taken out of the oil bath and cooled to room temperature in a water bath. After cooling, 200 g of water was added into the flask, and stirring was performed. After allowing it to stand, 8070 g of an organic phase was recovered.

Step (d)

The collected organic phase was distilled, thereby recovering 5800 g of DBC. The recovered DBC was analyzed by GC. As a result, it was confirmed that the purity of DBC was 99.8% and the content of a chlorine-containing compound was equal to or smaller than the lower limit of detection (1 ppm or less), as shown in Table 8.

TABLE 8

| | Content (GC area ratio vs DBC) | |
|---|---|---|
| Chemical structure | Before treatment | After treatment |
| $CCl_3C(=O)OCH_2CH_2CH_2CH_3$ | 5 ppm | <1 ppm |
| $CHCl_2C(=O)OCH_2CH_2CH_2CH_3$ | 2000 ppm | <1 ppm |
| $CH_2ClC(=O)OCH_2CH_2CH_2CH_3$ | 1 ppm | <1 ppm |

Examples 35 to 40

Decomposition Treatment Test

First, a carbonate test liquid used for a decomposition treatment test was prepared. DCAB synthesized in Example 4 was added to DBC purified to a high degree in Example 34, in an amount of 1000 ppm (mass concentration) based on DBC, thereby preparing the test liquid.

In a Pyrex (registered trademark)-made three-neck flask having internal volume of 300 mL were installed a stirring device, a Dimroth condenser in which a coolant cooled to 10° C. was circulated, and a rubber septum for sampling. In the flask was charged 150 g of the test liquid. Moreover, basic compounds shown in Table 9 were added thereto, and then the decomposition treatment test was performed by heating at a predetermined temperature with stirring. A portion of the content liquid was sampled at a predetermined time interval to analyze organic components by GC, and a decomposition rate of DCAB was evaluated. The change in DCAB concentration over time is shown in FIG. 1.

TABLE 9

| Ex. | Basic compound | Conjugate acid | Conjugate acid pKa | Mass ratio (base/DBC) | Temp. (° C.) |
|---|---|---|---|---|---|
| 35 | 10% aqueous NaOH solution | $H_2O$ | 15.7 | 1/99 | 80 |

TABLE 9-continued

| Ex. | Basic compound | Conjugate acid | Conjugate acid pKa | Mass ratio (base/DBC) | Temp. (° C.) |
|---|---|---|---|---|---|
| 36 | 10% aqueous NaOH solution | H$_2$O | 15.7 | 3/97 | 80 |
| 37 | 25% aqueous NaOH solution | H$_2$O | 15.7 | 1/99 | 80 |
| 38 | 10% aqueous KOH solution | H$_2$O | 15.7 | 1/2 | 20 |
| 39 | 25% aqueous K$_2$CO$_3$ solution | HCO$_3^-$ | 10.2 | 1/99 | 80 |
| 40 | (C$_2$H$_5$)$_3$N | (C$_2$H$_5$)$_3$NH$^+$ | 10.7 | 1/99 | 80 |

Example 41

Example of Producing DPC from DBC of Example 34

Production of DPC was conducted by a two-step reaction composed of an ester exchange reaction and a disproportionation reaction.

1. Ester Exchange Reaction:

For the ester exchange reaction, a vacuum jacket-attached packed glass-made column-type distillation column (inner diameter: 25 mmφ, filling material: Sulzer laboratory packing, theoretical stage number: 10 stages, not including a reboiler and a condenser) was used. A 5 L four-neck flask was mounted on the bottom of the distillation column, and there to was added a starting solution consisting of 1160 g of DBC, 1820 g of phenol and tetrabutyl titanate in an amount of 0.9 mol % based on DBC, followed by stirring with a magnetic stirring bar. The bottom of the column started to be heated in this state, and the temperature of the bottom of the column was increased up to 193° C. Thereafter, while a reflux ratio (R/D) was being varied from 0 to 36 to maintain the temperature of the top of the column at 117° C., 204 g of butanol was extracted from the top of the column in total. For the following reaction, 2790 g of the bottom liquid obtained at this time was used.

2. Disproportionation Reaction:

The disproportionation reaction was performed by using the bottom liquid of the above section 1 and using the same device as that of the section 1. The pressure of the system was slowly reduced from normal pressure to 100 mmHg with maintaining the temperature of the bottom of the column at 190 to 200° C., and 2360 g of a distillate containing phenol and DBC as main components was distilled away. In this manner, 420 g of a crude product containing about 50% of DPC was obtained as bottom liquid.

3. Purification:

The bottom liquid of the above section 2 was continuously put into a thin-film evaporator (manufactured by TOKYO RIKAKIKAI CO., LTD., MF-10C), and a high-boiling point substance containing a catalyst as a main component was removed at a temperature of 197° C. and a pressure of 2 mmHg. Thereafter, the obtained distillate was distilled under reduced pressure at a temperature of 180 to 200° C. and a pressure of 19 to 5 mmHg, thereby removing a low-boiling point component. Subsequently, distillation was performed again at a temperature of 180 to 200° C. and a pressure of 5 to 2 mmHg, thereby obtaining 80 g (GC purity of 99.9%) of purified DPC as a distillate.

Example 42

Example of Producing Aromatic Polycarbonate by Using DPC of Example 35

Into a 300 mL round bottom four-neck flask equipped with a distillation unit including an air-cooled tube (15 mmφ×200 mm) and a receiver, and equipped with a stirrer (manufactured by NAKAMURA SCIENTIFIC INSTRUMENTS INDUSTRY CO., LTD., MS-8) and a stirring blade were charged 31.19 g of BPA, 30.00 g (0.140 mol) of DPC, 31.19 g (0.137 mol) of BPA, and NaHCO$_3$ (1.0 μmol/BPA-mol) were put. The internal pressure of the system was reduced by using a rotary pump to dry for 1 hour. Thereafter, the pressure was increased to normal pressure by using nitrogen gas, and the flask was dipped in an oil bath at 180° C.

After the content was melted, polymerization was started at an oil bath temperature of 205° C. and a pressure of 200 mmHg. While the progress of polymerization was being checked from the amount of phenol generated in the system, the oil bath temperature and the internal pressure of the system were varied slowly. As conditions to be finally created, the oil bath temperature was set to 280° C., and the internal pressure of the system was set to be less than 1 mmHg. At a point in time when about 4 hours had passed from the beginning of polymerization and stirring could not be performed due to the increase in viscosity, polymerization was completed. The polymerized substance was almost colorless, and a mass average molecular weight Mw thereof was about 60000.

While the present invention has been described in detail and referring to specific embodiments, it is apparent for those skilled in the art that various modifications or changes can be made without departing from the spirit and scope of the present invention.

The present application is based on Japanese Patent Application No. 2012-178327 filed on Aug. 10, 2012, and the contents thereof are incorporated herein by reference.

INDUSTRIAL APPLICABILITY

According to the method for producing a carbonate compound of the present invention, it is possible to produce a high-purity carbonate compound usable for producing an aromatic polycarbonate, without using a toxic compound such as phosgene and without producing corrosive gas such as hydrogen chloride. The carbonate compound produced by the method for producing a carbonate compound of the present invention contains small amount of a chlorine-containing compound derived from hexachloroacetone used as a raw material and hence can be used as a medium of an electrolytic solution of a lithium ion battery for which intermixing of a chlorine-containing compound is not favorable.

The invention claimed is:

1. A method for producing a carbonate compound comprising: a first step of reacting a compound represented by the following Formula (1) with a compound represented by the following Formula (21) or a compound represented by the following Formula (22) to obtain a reaction mixture containing a carbonate compound, and a second step of bringing the reaction mixture containing a carbonate compound into contact with a strongly basic compound,

[Chem. 1]

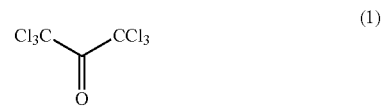

(1)

(21)

(22)

wherein R$^1$ represents a monovalent organic group, and R$^2$ represents a divalent organic group, wherein the reaction mixture comprising a compound represented by the following Formula (41) or a compound represented by the following Formula (42), and in the second step, the reaction mixture is brought into contact with the strongly basic compound to decompose the compound represented by the following Formula (41) or the compound represented by the following formula (42),

[Chem. 2]

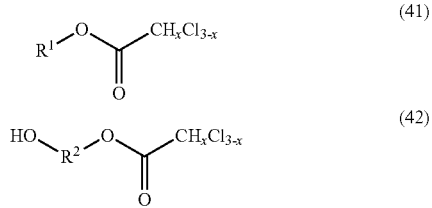

wherein x represents an integer of 0 to 2, and
the method obtains a carbonate compound in which a total content of the compounds represented by Formula (41) and the compounds represented by Formula (42) is 5 ppm or less based on the total amount of the carbonate compound, and
wherein the strongly basic compound is a salt of a base of which a conjugate acid has a pKa of 11 or higher and an alkali metal ion or an alkaline earth metal ion.

2. The method for producing a carbonate compound according to claim 1, wherein $R^1$ represents a monovalent aliphatic hydrocarbon group having 1 to 10 carbon atoms, and $R^2$ represents a divalent aliphatic hydrocarbon group having 1 to 10 carbon atoms.

3. The method for producing a carbonate compound according to claim 1, wherein in the second step, the reaction mixture is brought into contact with the strongly basic compound in the presence of an alcohol.

4. The method for producing a carbonate compound according to claim 1, wherein the strongly basic compound is a hydroxide or an alkoxide of an alkali metal or a hydroxide or an alkoxide of an alkaline earth metal.

5. The method for producing a carbonate compound according to claim 1, wherein in the first step, the compound represented by Formula (1) is reacted with the compound represented by Formula (21) or the compounds represented by Formula (22) in the presence of the following catalyst for synthesizing a carbonate compound: the catalyst for synthesizing a carbonate compound: one or more kinds selected from the group consisting of a weakly basic compound, a phase transfer catalyst, an ion exchange resin, and a compound or oxide of one or more kinds of metals selected from the group consisting of tin, titanium, aluminum, tungsten, molybdenum, zirconium, and zinc.

6. A method for producing diphenyl carbonate, comprising: preparing a carbonate compound by the method for producing a carbonate compound described in claim 1, and causing an ester exchange reaction between the obtained carbonate compound and phenol.

7. A method for producing an aromatic polycarbonate, comprising: preparing a diphenyl carbonate by the production method described in claim 6, and reacting the obtained diphenyl carbonate with a compound represented by the following Formula (6) in the presence of a catalyst for synthesizing a polycarbonate

[Chem. 3]

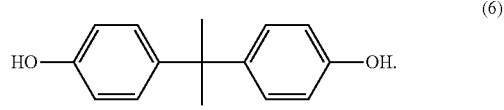

* * * * *